(12) United States Patent
Adachi et al.

(10) Patent No.: US 6,376,249 B1
(45) Date of Patent: Apr. 23, 2002

(54) METHOD FOR STABILIZING LOW-CONCENTRATION STANDARD REFERENCE GAS AND LOW-CONCENTRATION STANDARD REFERENCE GAS OBTAINED BY THE SAME

(75) Inventors: Fujio Adachi; Hirokazu Kawano, both of Yachiyo; Ichiro Misawa, Tokyo, all of (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days.

(21) Appl. No.: 09/337,497

(22) Filed: Jun. 22, 1999

Related U.S. Application Data

(63) Continuation-in-part of application No. 09/109,811, filed on Jul. 2, 1998, now abandoned.

(30) Foreign Application Priority Data

Jul. 7, 1997 (JP) .............................................. 9-181303
Jul. 3, 1998 (JP) ............................................ 10-188731

(51) Int. Cl.⁷ .............................................. G01N 31/00
(52) U.S. Cl. ................. 436/9; 436/8; 436/176; 436/181; 422/83; 422/99; 422/102; 422/939; 422/940; 134/22.1; 134/22.12; 134/22.18; 73/1.03

(58) Field of Search ................................ 436/8, 9, 176, 436/181; 422/83, 99, 102, 939, 940; 134/22.1, 22.12, 22.18, 26, 30, 36; 73/1.03

(56) References Cited

U.S. PATENT DOCUMENTS

| | | | | |
|---|---|---|---|---|
| 3,997,296 A | * | 12/1976 | Miller ............................ | 436/9 |
| 4,220,183 A | * | 9/1980 | Gökcek .......................... | 141/1 |
| 4,562,725 A | * | 1/1986 | Oka et al. .................... | 73/29.05 |
| 4,692,621 A | * | 9/1987 | Passaro et al. .............. | 250/343 |
| 4,723,436 A | * | 2/1988 | Moreth et al. ............... | 73/1.03 |
| 5,457,983 A | * | 10/1995 | Sauvageau et al. .......... | 73/1.03 |
| 5,885,361 A | * | 3/1999 | Kikuchi et al. .............. | 134/1.1 |

FOREIGN PATENT DOCUMENTS

| | | | |
|---|---|---|---|
| JP | 55-115694 | * | 9/1980 |
| JP | 63-57543 | * | 3/1988 |

* cited by examiner

*Primary Examiner*—Maureen M. Wallenhorst
(74) *Attorney, Agent, or Firm*—Michael D. Bednarek; Shaw Pittman LLP

(57) ABSTRACT

A method is provided for stabilizing a low-concentration standard reference gas. The stabilizing method includes the steps of treating an inner wall surface of a container with high-purity water for causing the inner wall surface to adsorb the high-purity water, and charging the container with the standard reference gas.

17 Claims, 1 Drawing Sheet

METHOD FOR STABILIZING LOW-CONCENTRATION STANDARD REFERENCE GAS AND LOW-CONCENTRATION STANDARD REFERENCE GAS OBTAINED BY THE SAME

This application is a continuation-in-part of application Ser. No. 09/109,811 filed Jul. 2, 1998, now abandoned.

BACKGROUND OF THE INVENTION

1. Field of the Invention

The present invention relates to a method for stabilizing a low-concentration standard reference gas, and a low-concentration standard reference gas obtained by such a method.

2. Description of the Related Art

In recent years, a variety of harmful substances are found at a low concentration in the atmosphere. Potential harm to the human health due to a long-time exposure to these substances has become a concern. Thus, it is necessary to monitor the concentration of these substances to see if the concentration exceeds a certain level.

In measurement of a harmful contaminant in the atmosphere, a greater reliability (measuring accuracy) is required as the quantity of the measured substance is smaller. Generally, the measurement is made by an analyzing instrument, and the reliability of the instrument must be maintained by periodically performing an accurate calibration with the use of an appropriate standard reference material. Specifically, a standard reference material containing a known concentration of harmful material is measured by the analyzing instrument which is then calibrated so that the measured concentration coincides with the known concentration of that harmful substance.

When the harmful substance is a gaseous component in the atmosphere, use is made of a standard reference gas containing that harmful substance as a component. In order for the calibration of the analyzing instrument to be made properly, the standard reference gas must be highly stable and accurate in its concentration level for a long time. However, because the standard reference gas is usually charged in a high-pressure gas container before supply, the gas component may react with the inner wall surface of the container and/or adsorbed by and desorbed from the inner wall surface of the container when the gas component is highly reactive and/or adsorptive, which leads to concentration fluctuations. Such concentration fluctuations are more significant as the concentration becomes lower.

Conventionally, for concentration stabilization of a gas component in a standard reference gas, the inner wall surface of a high-pressure gas container is treated by plating, coating or polishing. For example, Japanese Patent Publication 54-134070 discloses a method for stabilizing a standard reference gas by coating the inner wall surface of a high-pressure gas container with a natural or synthetic wax.

Further, in case where a standard reference gas contains a highly reactive gas component, the gas component is first charged in the container at a higher concentration (several times to several hundreds of times higher) than the target concentration, whereby the container is left for a certain period of time for aging to allow its inner wall surface to become sufficiently inactive. Then, an additional amount of the gas component is charged in the container together with a dilution gas to prepare a standard reference gas having a predetermined concentration of the gas component.

However, the above-described measures for stabilizing a standard reference gas cannot be used for a certain gas component. For example, a standard reference gas containing a trace quantity of acrylonitrile has been found to undergo great concentration fluctuations, thus failing to meet the requirements for a standard reference gas.

SUMMARY OF THE INVENTION

It is, therefore, an object of the present invention to provide a method for stabilizing a low-concentration standard reference gas which suffers only little concentration variation during long-term storage even if the standard reference gas contains such a gas component as acrylonitrile, and which is capable of exhibiting an accurate concentration of the gas component especially in a low-concentration range.

Another object of the present invention is to provide a low-concentration standard reference gas obtained by such a method.

According to a first aspect of the present invention, there is provided a method for stabilizing a low-concentration standard reference gas comprising the steps of: treating an inner wall surface of a container with high-purity water for causing the inner wall surface to adsorb the high-purity water; and charging the container with the standard reference gas.

With the stabilization method described above, the inner wall surface of the container is pre-treated with high-purity water. Because of this pretreatment, the molecules of high-purity water are adsorbed and held by the inner wall surface of the container in a thermodynamically stable state. Thus, when a standard reference gas containing a trace quantity of gas component is charged later into the container, the molecules of the gas component will not replace the water molecules which have been previously adsorbed, nor will they react with the inner wall surface of the container. As a result, the concentration of the gas component in the standard reference gas is kept stable for a long period of time.

The step for adsorption may comprise evacuating the container to a vacuum of not higher than 13 Pa, and vaporizing under said vacuum 2~23 mg, preferably 4.75~23 mg, of high-purity water per 1 $dm^3$ of volumetric capacity of the container. If the amount of water is less than 2 mg, water adsorption cannot cover the entire inner wall surface of the container. The amount of water exceeding 23 mg does not further improve the effectiveness of the adsorption treatment while deteriorating the stability of the gas component concentration.

The purity of water to be used in the method of the present invention should be as high as possible. Generally, satisfactory results maybe obtained when the high-purity water has a specific resistance of not lower than $0.1 \times 10^6$ Ω·cm, preferably $10 \times 10^6$ Ω·cm, particularly $16 \times 10^6$ Ω·cm. It should be noted here that the specific resistance is a measure representing the purity of water. A higher specific resistance indicates a higher purity, containing a smaller amount of impurities such as ions. There is no upper limit for the specific resistance of high-purity water, but in practice the specific resistance is limited to somewhere around $18 \times 10^6$ Ω·cm due to the ability of a super high-purity water system.

Typically, the standard reference gas may contain at least one gas component selected from a group consisting of acrylonitrile, 1,3-butadiene, formaldehyde, vinyl chloride, dichloromethane, chloroform, 1,2-dichloroethane, benzene, tricholoroethylene, and tetrachloroethylene. Excellent results may be obtained when the standard reference gas contains acrylonitrile, 1,3-butadiene and formaldehyde.

Further, the stabilization method according to the present invention become more remarkable as the concentration of the gas component in the standard reference gas is lower. Specifically, the concentration of the gas component may be preferably in the range of 0.001 to 100 ppm.

The container may be made of an alloy selected from a group consisting of an aluminum alloy and a manganese steel. Further, the inner wall surface of the container may be polished.

According to a second aspect of the present invention, there is provided a combination of a low-concentration standard reference gas and a container containing the standard reference gas, wherein the container having an inner wall surface which has adsorbed high-purity water.

The other objects, features and advantages of the present invention will become clear from the following description of the preferred embodiment given with reference to the accompanying drawings.

BRIEF DESCRIPTION OF THE DRAWINGS

The single drawing (FIG. 1) is a schematic diagram showing a high-purity water adsorption system to be used in the method according to the present invention.

DETAILED DESCRIPTION OF THE PREFERRED EMBODIMENT

Figure 1:
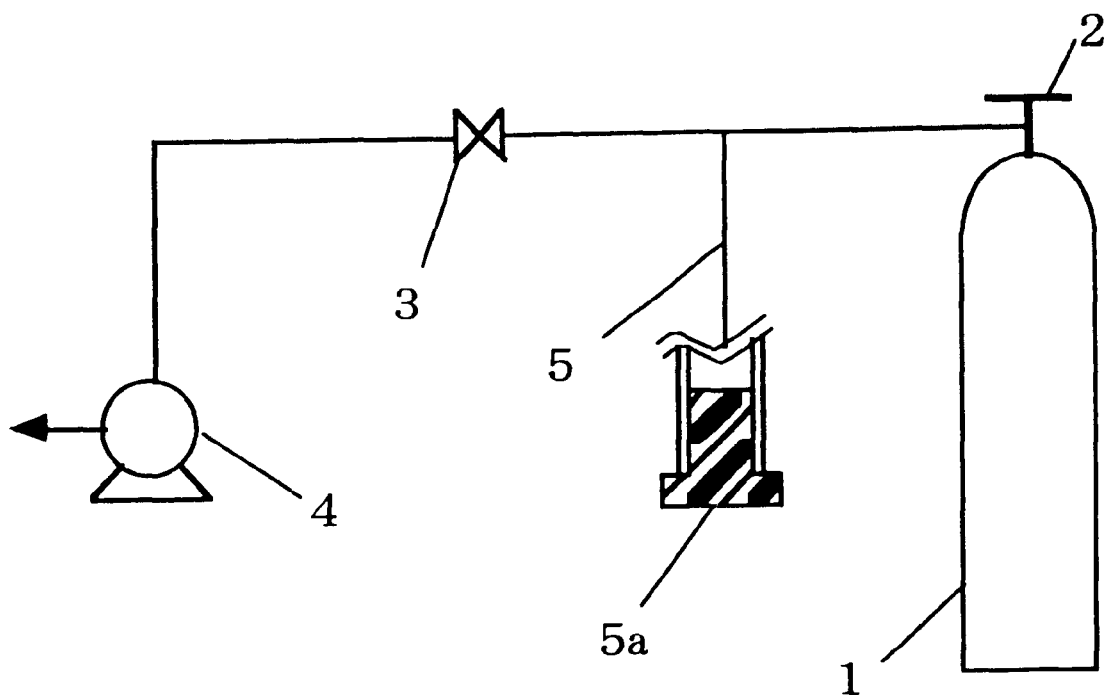

A preferred embodiment of the present invention will be described below with reference to the accompanying drawing.

Referring now to FIG. 1, a gas cylinder 1 (as an example of container) has a inlet-outlet valve 2 which is piped to a vacuum pump 4 via an on-off valve 3. On the other hand, a branch line 5 is connected to the piping between the inlet-outlet valve 2 and the on-off valve 3. The branch line 5 has a non-connected end which is closed by a sealing member 5a made of an elastic material such as a silicone rubber. In FIG. 1, the non-connected end alone of the branch line 5 is shown in an enlarged scale.

The gas cylinder 1 is usually made of an aluminum alloy or a manganese steel, and the inner wall surface of the gas cylinder is polished. Specifically, the gas cylinder 1 may be a seamless gas cylinder made of #6061 alloy (an example of aluminum alloy) listed in JIS (Japanese Industrial Standards) H0001-79 or of STH 750 (an example of manganese steel) listed in JIS G3429.

With the above arrangement, a stabilization method according to the present invention may be carried out in the following manner. Specifically, with the inlet-outlet valve 2 and the on-off valve 3 held open, the vacuum pump 4 is operated to evacuate the gas cylinder 1 to a vacuum of not higher than 13 Pa (0.1 mmHg), preferably not higher than 1.3 Pa (0.01 mmHg). When the desired vacuum is achieved, the on-off valve 3 is closed. While the inlet-outlet valve 2 is still open, a syringe for example is driven into the sealing member 5a for injecting a predetermined amount of high-purity water through the branch line 5 into the gas cylinder 1. The sealing member 5a has sufficient elasticity and air-tightness for preventing air ingress during the water injection.

The high-purity water injected into the gas cylinder 1 vaporizes immediately under the high vacuum, and then adsorbed by the inner wall surface of the gas cylinder. A portion of high-purity water which has not been adsorbed stays in the gas cylinder in the gas phase. However, the chemical inactivity of the high-purity water relative to the co-existing gas components will not cause any adverse affect on the subsequent analysis.

When the adsorption treatment of the inner wall surface finishes, th e gas cylinder 1 is detached from the piping system for the adsorption treatment. Then, the gas cylinder 1 is charged with a standard reference gas having a predetermined low-concentration. Usually, the low-concentration standard reference gas is charged at a pressure of 1 MPa (10 $kg/cm^2$) to 15 MPa (150 $kg/cm^2$).

Alternatively, instead of directly charging a predetermined low-concentration standard reference gas, a gas mixture having a 100-times concentration for example may be charged at 0.1 MPa (1 $kg/cm^2$) for example, and then a diluent gas such as nitrogen may be charged to a pressure of 10 MPa (100 $kg/cm^2$) to prepare a predetermined low-concentration standard reference gas held at 10 MPa.

EXAMPLES

Next, more specific examples of the present invention will be described together with comparative examples. However, the present invention is not limited to those examples. Further, the analysis was performed in the following manner.

[Method of Analysis]

The analysis of a low-concentration standard reference gas containing acrylonitrile and/or 1,3-butadiene as a component was performed by programmed temperature chromatography using a gas chromatograph provided with a flame ionization detector (FID). For preparing a separation column, a methyl silicone liquid phase was used with a coated capillary tube.

And in the case which a low-concentration standard reference gas containing formaldehyde as a component, the analysis was performed by first contacting a low concentration standard gas containing formaldehyde with an oxidation catalyst to convert formaldehyde to carbon dioxide followed by methanating to methane, and analyzed the resultant methane using a gas chromatograph provided with a flame ionization detector (FID). For preparing a separation column, an active carbon was used instead of a methyl silicone liquid phase.

Example 1

An aluminum alloy gas cylinder 1 having a capacity of 10 $dm^3$ was evacuated to a vacuum of not higher than 1.33 Pa (0.01 mmHg) at room temperature (25° C.). The interior of the gas cylinder 1 was restored to the atmospheric pressure by introducing high-purity nitrogen (99.9995% purity). After repeating these steps several times, the gas cylinder 1 was maintained at a vacuum of 1.33 Pa (0.01 mmHg). 50 mg of high-purity water (having a specific resistance of $18 \times 10^6$ Ω·cm) drawn into a microsyringe was injected through the sealing member 5a into the gas cylinder 1 held under vacuum. After the water injection, the pressure in the gas cylinder 1 increased 559 Pa (4.2 mmHg).

Then, nitrogen gas containing 1 ppm of acrylonitrile was charged through the inlet-outlet valve 2 into the gas cylinder 1 to a pressure of 12 MPa (120 $kg/cm^2$). Analysis was made for variations of the acrylonitrile concentration at three different points of time which include (1) right after the charging, (2) one month after the charging, and three months after the charging. The results are shown in Table 1 below.

TABLE 1

| Number | Injected Water (mg/dm$^3$) | Gas Component | Analysis Results (PPM) Right after | One month | Three months | Container material |
|---|---|---|---|---|---|---|
| Example 1 | 5 | acrylonitrile | 0.99 | 1.00 | 0.98 | Al Alloy |
| Example 2 | 20 | acrylonitrile | 1.01 | 0.97 | 0.99 | Al Alloy |
| Example 3 | 5 | acrylonitrile | 0.98 | 1.02 | 0.97 | Al Alloy |
|  |  | 1,3-butadiene | 1.01 | 0.97 | 0.97 |  |
| Example 4 | 20 | acrylonitrile | 1.03 | 0.97 | 0.97 | Al Alloy |
|  |  | 1,3-butadiene | 0.99 | 0.97 | 0.96 |  |
| Example 5 | 20 | acrylonitrile | 102 | 98 | 97 | Al Alloy |
|  |  | 1,3-butadiene | 99 | 98 | 96 |  |
| Example 6 | 5 | acrylonitrile | 1.03 | 1.04 | 1.02 | Mn Steel |
| Example 7 | 5 | formaldehyde | 10.3 | 10.3 | 10.4 | Al Alloy |
| Comp. 1 | None | acrylonitrile | 0.42 | 0.13 | 0.05 | Al Alloy |
| Comp. 2 | 50 | acrylonitrile | 0.51 | 0.21 | 0.10 | Al Alloy |
| Comp. 3 | None | acrylonitrile | 63 | 52 | 36 | Al Alloy |
|  |  | 1,3-butadiene | 68 | 42 | 22 |  |

As clearly shown in Table 1, the concentration of acrylonitrile was stable with the measurements within tolerance even after the 3 months had passed.

Example 2

In Example 2, the same adsorption treatment as in Example 1 was performed except that the amount of high-purity water was 200 mg, and the degree of vacuum was 1.0 Pa (0.0075 mmHg). After the water injection, the pressure in the gas cylinder 1 increased to 2.9 kPa (22 mmHg). Then, nitrogen gas containing 100 ppm of acrylonitrile was charged into the gas cylinder 1 to a pressure of 0.1 MPa (1 kg/cm$^2$). Then, high-purity nitrogen gas was charged to an increased pressure of 10 MPa (100 kg/cm$^2$).

The standard reference gas thus prepared to contain 1 ppm of acrylonitrile was analyzed in the same manner as in Example 1. The results are also shown in Table 1 from which it is understood that the concentration of acrylonitrile was stable with the measurements within tolerance even after 3 months had passed.

Example 3

An aluminum alloy gas cylinder 1 having a capacity of 10 dm$^3$ was treated in the same manner as in Example 1. Nitrogen gas containing 1 ppm of acrylonitrile and 1 ppm of 1,3-butadiene was charged through the inlet-outlet valve 2 to a pressure of 10 MPa (100 kg/cm$^2$).

The standard reference gas thus prepared to contain the two gas components (other than nitrogen) was analyzed in the same manner as in Example 1. The results are also shown in Table 1 which indicates that the respective concentration of acrylonitrile and 1,3-butadiene was equally stable with the measurements within tolerance even after 3 months had passed.

Example 4

The aluminum alloy gas cylinder 1 having a capacity of 10 dm$^3$ was treated in the same manner as in Example 2. Nitrogen gas containing 100 ppm of acrylonitrile and 100 ppm of 1,3-butadiene was charged through the inlet-outlet valve 2 to a pressure of 0.1 MPa (1 kg/cm$^2$). Then, the pressure was increased to 10 MPa (100 kg/cm$^2$) by charging high-purity nitrogen gas.

The standard reference gas thus prepared to contain the two gas components (other than nitrogen) was analyzed in the same manner as in Example 1. The results are also shown in Table 1 from which it is appreciated that the respective concentration of acrylonitrile and 1,3-butadiene was equally stable with the measurements within tolerance even after 3 months had passed.

Example 5

An aluminum alloy gas cylinder 1 having a capacity of 10 dm$^3$ was treated in the same manner as in Example 2. The nitrogen gas containing 100 ppm of acrylonitrile and 100 ppm of 1,3-butadiene was charged through the inlet-outlet valve 2 to a pressure of 10 MPa (100 kg/cm$^2$).

The standard reference gas thus prepared to contain the two gas components other than nitrogen was analyzed in the same manner as in Example 1. The results are also shown in Table 1 which reveals that the respective concentration of acrylonitrile and 1,3-butadiene was equally stable with the measurements within tolerance even after 3 months had passed.

Example 6

The same adsorption treatment as in Example 1 was performed except that a gas cylinder 1 made of a manganese steel in which an inner wall surface was polished was used instead of the aluminum alloy gas cylinder. After the adsorption treatment, nitrogen gas containing 1 ppm of acrylonitrile was charged through the inlet-outlet valve 2 to a pressure of 12 MPa (120 kg/cm$^2$).

The standard reference gas thus prepared was analyzed in the same manner as in Example 1. The results are also shown in Table 1 from which it is understood that the concentration of acrylonitrile was stable with the measurements within tolerance even after 3 months had passed.

Example 7

The aluminum alloy gas cylinder 1 having a capacity of 10 dm$^3$ was treated in the same manner as in Example 1. Nitrogen gas containing 10 ppm of formaldehyde was charged through the inlet-outlet valve 2 to a pressure of 5 MPa (50 kg/cm$^2$).

The standard reference gas thus prepared was analyzed in the manner as described before. The results are also shown in Table 1 from which it is understood that the concentration of formaldehyde was stable with the measurements within tolerance even after 3 months had passed.

Comparison 1

An aluminum alloy gas cylinder 1 having a capacity of 10 dm$^3$ was evacuated to a vacuum of not higher than 1.33 Pa (0.01 mmHg) at room temperature (25° C.). Then, the pressure of the gas cylinder 1 was restored to the atmospheric pressure by introducing high-purity nitrogen (99.9995% purity). After repeating these steps several times, the vacuum was kept at 1.33 Pa (0.01 mmHg). Then, without injecting high-purity water, nitrogen gas containing 1 ppm of acrylonitrile was charged through the inlet-outlet valve 2 to a pressure of 12 MPa (120 kg/cm$^2$).

An analysis was made for variations of the acrylonitrile concentration in the same manner as in Example 1. The results are also shown in Table 1 which clearly shows that the concentration of acrylonitrile decreased with time.

Comparison 2

The same adsorption treatment as in Example 1 was performed except that the amount of high-purity water was increased to 500 mg. Then, nitrogen gas containing 1 ppm of acrylonitrile was charged through the inlet-outlet valve 2 for obtaining a standard reference gas held at a pressure of 12 MPa (120 kg/cm$^2$).

An analysis was made for variation of the acrylonitrile concentration in the same manner as in Example 1. The results are also shown in Table 1 from which it is understood that the concentration of acrylonitrile decreased with time.

Comparison 3

The same process steps as in Comparison 1 were performed except that, instead of nitrogen gas containing 1 ppm of acrylonitrile, nitrogen gas containing 100 ppm of acrylonitrile and 100 ppm of 1,3-butadiene was charged for preparing a standard reference gas containing the two gas components at a pressure of 12 MPa (120 kg/cm$^2$).

An analysis was made for the variations of the respective concentration of the two gas components in the same manner as in Example 1. The results are also shown in Table 1 which indicates that the respective concentration of both acrylonitrile and 1,3-butadiene decreased significantly right after the charging and continued to decrease with time.

As has been described hereinabove, according to the present invention, it is possible to stabilize the concentration of a gas component by treating a gas cylinder with high-purity water, and charging a standard reference gas containing a trace quantity of a gas component. Therefore, it has become possible to stably supply a standard reference gas containing a low-concentration gas component necessary for monitoring air pollution for example.

The preferred embodiment of the present invention being thus described, it is obvious that the same may be varied in various ways. Such variations should not be regarded as a departure from the spirit and scope of the invention, and all such variations as would be obvious to those skilled in the art are intended to be included within the scope of the appended claims.

What is claimed is:

1. A method for stabilizing a standard reference gas comprising the steps of:

treating an inner wall surface of a container with vaporized water for causing the inner wall surface to adsorb the vaporized water; and charging the container with the standard reference gas;

wherein the standard reference gas is stabilized by the adsorbed, vaporized water which prevents the adsorption of the standard reference gas onto the inner wall surface of the container; and wherein the step for adsorption comprises evacuating the container to a vacuum of not higher than 13 Pa, and vaporizing under said vacuum 2~23 mg of water per 1 dm$^3$ of volumetric capacity of the container.

2. The method according to claim 1, wherein the container is made of an alloy selected from a group consisting of an aluminum alloy and a manganese steel.

3. The method according to claim 2, wherein the inner wall surface of the container is polished.

4. A method for stabilizing a standard reference gas comprising the steps of:

treating an inner wall surface of a container with vaporized water for causing the inner wall surface to adsorb the vaporized water; and charging the container with the standard reference gas;

wherein the standard reference gas is stabilized by the adsorbed, vaporized water which prevents the adsorption of the standard reference gas onto the inner wall surface of the container; and wherein the water has a specific resistance of not lower than 0.1×10$^6$ Ω·cm.

5. A method for stabilizing a standard reference gas comprising the steps of:

treating an inner wall surface of a container with vaporized water for causing the inner wall surface to adsorb the vaporized water; and charging the container with the standard reference gas;

wherein the standard reference gas is stabilized by the adsorbed, vaporized water which prevents the adsorption of the standard reference gas onto the inner wall surface of the container; and wherein the standard reference gas contains at least one gas component selected from a group consisting of acrylonitrile, 1,3-butadiene, formaldehyde, vinyl chloride, dichloromethane, chloroform, 1,2-dichloroethane, benzene, tricholoroethylene, and tetrachloroethylene.

6. The method according to claim 5, wherein said at least one gas component is acrylonitrile.

7. The method according to claim 5, wherein said at least one gas component is 1,3-butadiene.

8. The method according to claim 5, wherein said at least one gas component is formaldehyde.

9. The method according to claim 5, wherein said at least one gas component is contained at a concentration of 0.001 to 100 ppm.

10. A combination comprising a standard reference gas and a container containing the standard reference gas, wherein the container has an inner wall surface on which vaporized water is adsorbed for preventing the adsorption of the standard reference gas onto the inner wall surface of the container;

wherein the water has a specific resistance of not lower than 0.1×10$^6$ Ω·cm.

11. The combination according to claim 10, wherein the container is made of an alloy selected from a group consisting of an aluminum alloy and a manganese steel.

12. The combination according to claim 11, wherein the inner wall surface of the container is polished.

13. A combination comprising a standard reference gas and a container containing the standard reference gas, wherein the container has an inner wall surface on which vaporized water is adsorbed for preventing the adsorption of the standard reference gas onto the inner wall surface of the container;

wherein the standard reference gas contains at least one gas component selected from a group consisting of acrylonitrile, 1,3-butadiene, formaldehyde, vinyl chloride, dichloromethane, chloroform, 1,2-dichloroethane, benzene, tricholoroethylene, and tetrachloroethylene.

14. The combination according to claim 13, wherein said at least one gas component is acrylonitrile.

15. The combination according to claim 13, wherein said at least one gas component is 1,3-butadiene.

16. The combination according to claim 13, wherein said at least one gas component is formaldehyde.

17. The combination according to claim 13, wherein said at least one gas component is contained at a concentration of 0.001 to 100 ppm.

* * * * *